US00PP10660P

United States Patent [19]

Warren

[11] Patent Number: Plant 10,660

[45] Date of Patent: Oct. 27, 1998

[54] STOKESIA PLANT NAMED 'PURPLE PARASOLS'

[76] Inventor: Clyde Scott Warren, 1559 Connor Rd., Hebron, Ky. 41048

[21] Appl. No.: 828,652

[22] Filed: Mar. 31, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—C. A. Whealy

[57] ABSTRACT

A distinct cultivar of Stokesia plant named 'Purple Parasols', characterized by its vigorous plant growth habit and moderate growth rate; large, showy inflorescences; ray florets that initially are light blue, becoming darker blue, then bluish purple to reddish purple and dark hot pink with further development; numerous inflorescences per plant; and good container, cut flower and garden performance.

1 Drawing Sheet

The present invention relates to a new and distinct cultivar of Stokesia plant, botanically known as *Stokesia cyanea*, and hereinafter referred to by the cultivar name Purple Parasols.

The new cultivar was discovered by the inventor in the summer of 1993 as a naturally-occurring mutation of a seed-produced unidentified selection of *Stokesia cyanea* in a greenhouse in Hebron, Ky.

Asexual reproduction of the new cultivar by divisions taken at Hebron, Ky., has shown that the unique features of this new Stokesia are stable and reproduced true to type in successive generations.

The cultivar Purple Parasols has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Purple Parasols'. These characteristics in combination distinguish 'Purple Parasols' as a new and distinct cultivar:

1. Vigorous plant growth habit and moderate growth rate.
2. Large, showy inflorescences.
3. Ray florets that intially are light blue, becoming darker blue, then bluish purple to reddish purple and dark hot pink with further development.
4. Numerous inflorescences per plant.
5. Good container, cut flower and garden performance.

The new Stokesia can be compared to the commercial nonpatented Stokesia cultivar Blue Danube. However, in side-by-side comparisons conducted in Hebron, Ky., the new Stokesia has more inflorescences, larger and taller inflorescences, longer lasting inflorescences, and seeds produced are smaller in diameter. In addition, the ray floret color of the new Stokesia changes from light blue to bluish purple to redddish purple to dark hot pink whereas the ray floret color of plants of the cultivar Blue Danube is typically light blue.

The accompanying colored photograph illustrates the appearance of the new cultivar, showing the colors as true as it is reasonably possible to obtain in colored reproductions of this type. The photograph comprises a close-up view of typical mature inflorescences of 'Purple Parasols'. Flower and foliage colors in the photograph may appear different from the actual colors due to light reflectance.

In the following description, color references are made to The Royal Horticultural Society Colour Chart except where general terms of ordinary dictionary significance are used. The following observations, measurements and numerical values were taken from typical containerized plants grown in Hebron, Ky.; Mount Vernon, Wash.; and Keller, Tex.

during the spring and summer under outdoor production practice.

Botanical classification: *Stokesia cyanea* cultivar Purple Parasols.

Commercial classification: Perennial garden, cut flower, or containerized plant.

Parentage: Naturally-occurring mutation of a seed-produced unidentified selection of *Stokesia cyanea.*

Propagation:

*Type.*—By division.

*Time to initiate roots.*—Usually 20 to 30 days at 21° C.

*Rooting habit.*—Numerous and fibrous.

Plant description:

*Appearance.*—Perennial herbaceous decorative garden, cut flower or containerized plant. Uniform mounted plant habit. During periods of cool temperatures, flowering stems are longer and more upright than during the summer.

*Plant size.*—Height at flowering: 15 to 30 cm. Plant height or spread: About 65 cm.

*Vigor.*—Vigorous and moderate growth rate.

*Crop time.*—About 22 weeks are required from a rooted plant to a finished, flowering 15-cm garden container.

*Foliage description.*—Length: Up to 25 cm. Width: About 4 cm. Shape: Oblong-lanceolate or spatulate with pointed apex and attenuate base. Margin: Entire. Texture: Glabrous and dull, pronounced midrib on abaxial surface. Color: Young foliage, adaxial surface: 141A. Young foliage, abaxial surface: 141C. Mature foliage, adaxial surface: 135A. Mature foliage, abaxial surface: 138B. Venation color, adaxial surface: 145C. Venation color, abaxial surface: 145C. Petiole: 135A overlaid with 187B. Petiole: Length: 3 to 6 mm. Width: 3 to 6 mm.

Flower description:

*Flower type and habit.*—Single flowers arranged in corymbs. Freely flowering, very floriferous with new buds continuing to develop from spring through fall.

*Natural flowering season.*—Spring through fall in Northern Hemisphere. Flowers persistent.

*Inflorescences borne.*—Above foliage, arising from leaf axils.

*Time to flower.*—Under typical spring/summer growing temperatures, plants of the new Stokesia will start flowering 18 to 24 weeks after propagation.

*Inflorescence longevity.*—On the plant, inflorescences usually last one to three weeks depending on temperature. As a cut flower, inflorescences maintain good substance for about two weeks under interior conditions.

*Inflorescence diameter.*—5 to 12 cm.

*Inflorescence depth (height).*—2.5 to 5 cm.

*Quantity.*—Usually 25 to 50 inflorescences are formed per plant during the flowering season.

*Inflorescence aspect.*—Upright, usually perpendicular to the peduncle.

*Inflorescence buds.*—Length: 2 to 4 cm. Diameter: 2 to 4 cm. Shape: Rounded. Rate of opening: 2 to 3 days from tight bud to open flower. Color: 141A to 141C.

*Ray florets.*—Shape: Pleated, elongated, enlarging at apex, apex dentate. Size: Length: 1.25 to 2 cm. Width: 3 to 9 mm. Margin: Entire. Texture: Satiny and glabrous. Number of ray florets per inflorescence: 16 to 26. Color: Ray floret color changes as inflorescences open and develop. Color changes occur one to three days depending on temperature with color changes occurring more rapidly under higher temperatures.

When opening: Going from light blue, 109B, to medium blue, 105B, to dark blue, 104A. Mature: Going from bluish purple, 96A, to blue purple, 90A, to red purple, 87A, to reddish purple, 64A, to purplish red, 66A, to dark hot pink, 80A.

*Peduncle.*—Aspect: Strong and erect. Length: 5 to 10 cm. Color: 135A overlaid with 187B.

*Sepals.*—Appearance: Pleated, entire and serrate margins, apex, acute. Quantity: 16 to 26. Shape: Lanceolate. Color: Adaxial surface: 141A. Abaxial surface: 141C.

*Reproductive organs.*—Androecium: Quantity: 40 to 60. Anther color: White. Pollen: Trace, white in color. Gynoecium: Quantity: 40 to 60. Pistil length: 0.5 to 1 mm. Stigma shape: Tubular. Stigma color: 155B. Style length: 1 to 2 mm. Style color: 155B. Ovary color: 157C.

Disease resistance: Similar to other Stokesias, leaf spot is occasionally observed.

Seed production:

*Size.*—Length: About 0.2 mm. Diameter: About 0.1 mm. Color: 199D.

It is claimed:

1. A new and distinct cultivar of Stokesia plant named 'Purple Parasols', as illustrated and described.

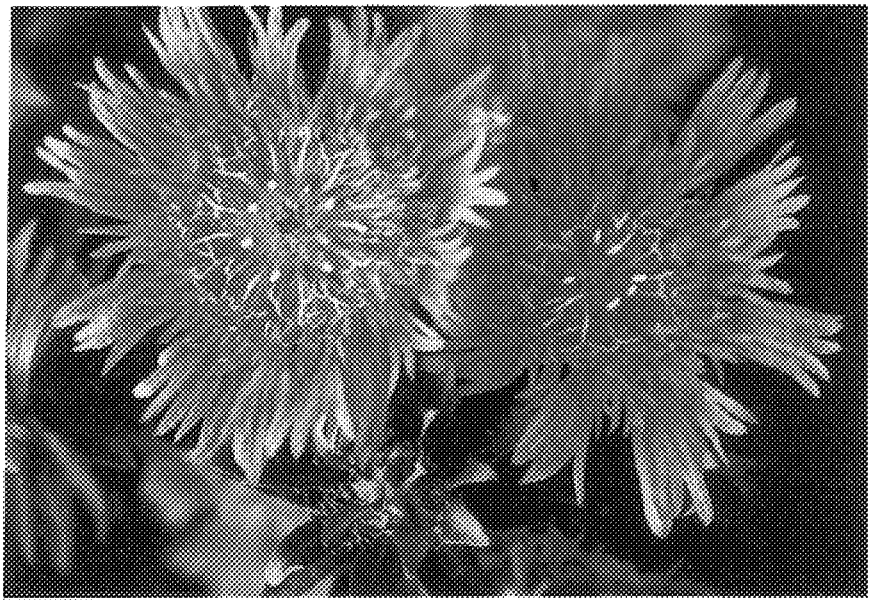

* * * * *